(12) United States Patent
Akery

(10) Patent No.: US 8,170,177 B2
(45) Date of Patent: *May 1, 2012

(54) MULTIPLE PASS CARGO INSPECTION SYSTEM

(75) Inventor: Alan Akery, Crawley (GB)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/952,180

(22) Filed: Nov. 22, 2010

(65) Prior Publication Data

US 2011/0127426 A1 Jun. 2, 2011

Related U.S. Application Data

(63) Continuation of application No. 12/404,913, filed on Mar. 16, 2009, now Pat. No. 7,860,213, which is a continuation of application No. 11/744,411, filed on May 4, 2007, now Pat. No. 7,526,064.

(60) Provisional application No. 60/746,540, filed on May 5, 2006.

(51) Int. Cl.
*G01N 23/04* (2006.01)

(52) U.S. Cl. .......................................... 378/57; 378/198

(58) Field of Classification Search ............... 378/51, 378/57, 146, 198
See application file for complete search history.

(56) References Cited

U.S. PATENT DOCUMENTS

| | | | |
|---|---|---|---|
| 2,831,123 A | 4/1958 | Daly | |
| 3,766,387 A | 10/1973 | Heffan et al. | |
| 3,784,837 A | 1/1974 | Holmstrom | |
| RE28,544 E | 9/1975 | Stein et al. | |
| 4,047,035 A | 9/1977 | Dennhoven et al. | |
| 4,139,771 A | 2/1979 | Dennhoven et al. | |
| 4,210,811 A | 7/1980 | Dennhoven et al. | |
| 4,216,499 A | 8/1980 | Kunze et al. | |
| 4,366,382 A | 12/1982 | Kotowski | |
| 4,430,568 A | 2/1984 | Yoshida et al. | |
| 4,566,113 A | 1/1986 | Donges et al. | |
| 4,599,740 A | 7/1986 | Cable | |
| 4,641,330 A | 2/1987 | Herwig et al. | |
| 4,736,401 A | 4/1988 | Donges et al. | |
| 4,788,704 A | 11/1988 | Donges et al. | |
| 4,825,454 A | 4/1989 | Annis et al. | |
| 4,884,289 A | 11/1989 | Glockmann et al. | |
| 4,979,202 A | 12/1990 | Siczek et al. | |
| 4,991,189 A | 2/1991 | Boomgaarden et al. | |
| 5,022,062 A | 6/1991 | Annis | |
| 5,065,418 A | 11/1991 | Bermbach et al. | |
| 5,091,924 A | 2/1992 | Bermbach et al. | |
| 5,098,640 A | 3/1992 | Gozani et al. | |
| 5,179,581 A | 1/1993 | Annis | |
| 5,181,234 A | 1/1993 | Smith | |
| 5,182,764 A | 1/1993 | Peschmann et al. | |
| 5,224,144 A | 6/1993 | Annis | |

(Continued)

*Primary Examiner* — Courtney Thomas
(74) *Attorney, Agent, or Firm* — Novel IP

(57) ABSTRACT

The present invention is a cargo inspection system, employing a radiation source, capable of scanning vehicles and/or cargo in a wide range of sizes, including conventional imaging areas as well as taller and bulkier enclosures at sufficiently optimal efficacy and overall throughput. In one embodiment, the present invention is a multiple pass inspection method for inspecting vehicles and their cargo, comprising a first pass scan, wherein said first pass scan includes moving a radiation source at a suitable scanning distance, rotating a radiation source at a suitable scanning angle, and moving said radiation source along an object under inspection.

20 Claims, 12 Drawing Sheets

U.S. PATENT DOCUMENTS

| | | | |
|---|---|---|---|
| 5,237,598 A | 8/1993 | Albert | |
| 5,247,561 A | 9/1993 | Kotowski | |
| 5,253,283 A | 10/1993 | Annis et al. | |
| 5,313,511 A | 5/1994 | Annis et al. | |
| 5,367,552 A | 11/1994 | Peschmann | |
| 5,379,334 A | 1/1995 | Zimmer et al. | |
| 5,493,596 A | 2/1996 | Annis | |
| 5,638,420 A | 6/1997 | Armistead | |
| 5,642,393 A | 6/1997 | Krug et al. | |
| 5,642,394 A | 6/1997 | Rothschild | |
| 5,666,393 A | 9/1997 | Annis | |
| 5,687,210 A | 11/1997 | Maitrejean et al. | |
| 5,692,028 A | 11/1997 | Geus et al. | |
| 5,751,837 A | 5/1998 | Watanabe et al. | |
| 5,764,683 A | 6/1998 | Swift et al. | |
| 5,768,334 A | 6/1998 | Maitrejean et al. | |
| 5,787,145 A | 7/1998 | Geus | |
| 5,805,660 A | 9/1998 | Perion et al. | |
| 5,838,759 A | 11/1998 | Armistead | |
| 5,903,623 A | 5/1999 | Swift et al. | |
| 5,910,973 A | 6/1999 | Grodzins | |
| 5,930,326 A | 7/1999 | Rothschild et al. | |
| 5,940,468 A | 8/1999 | Huang et al. | |
| 5,974,111 A | 10/1999 | Krug et al. | |
| 6,031,890 A | 2/2000 | Bermbach et al. | |
| 6,058,158 A | 5/2000 | Eiler | |
| 6,067,344 A | 5/2000 | Grodzins et al. | |
| 6,081,580 A | 6/2000 | Grodzins et al. | |
| 6,094,472 A | 7/2000 | Smith | |
| 6,151,381 A | 11/2000 | Grodzins et al. | |
| 6,188,747 B1 | 2/2001 | Geus et al. | |
| 6,192,101 B1 | 2/2001 | Grodzins | |
| 6,192,104 B1 | 2/2001 | Adams | |
| 6,195,413 B1 | 2/2001 | Geus et al. | |
| 6,198,795 B1 | 3/2001 | Naumann et al. | |
| 6,218,943 B1 | 4/2001 | Ellenbogen | |
| 6,249,567 B1 | 6/2001 | Rothschild et al. | |
| 6,252,929 B1 | 6/2001 | Swift et al. | |
| 6,256,369 B1 | 7/2001 | Lai | |
| 6,278,115 B1 | 8/2001 | Annis et al. | |
| 6,282,260 B1 | 8/2001 | Grodzins | |
| 6,292,533 B1 | 9/2001 | Swift et al. | |
| 6,301,326 B2 | 10/2001 | Bjorkholm | |
| 6,320,933 B1 | 11/2001 | Grodzins et al. | |
| 6,356,620 B1 | 3/2002 | Rothschild et al. | |
| 6,424,695 B1 | 7/2002 | Grodzins et al. | |
| 6,434,219 B1 | 8/2002 | Rothschild et al. | |
| 6,435,715 B1 | 8/2002 | Betz et al. | |
| 6,442,233 B1 | 8/2002 | Grodzins et al. | |
| 6,445,765 B1 | 9/2002 | Frank et al. | |
| 6,453,003 B1 | 9/2002 | Springer et al. | |
| 6,453,007 B2 | 9/2002 | Adams et al. | |
| 6,456,684 B1 | 9/2002 | Mun et al. | |
| 6,459,761 B1 | 10/2002 | Grodzins et al. | |
| 6,459,764 B1 | 10/2002 | Chalmers | |
| 6,473,487 B1 | 10/2002 | Le | |
| RE37,899 E | 11/2002 | Grodzins et al. | |
| 6,483,894 B2 | 11/2002 | Hartick et al. | |
| 6,507,025 B1 | 1/2003 | Verbinski et al. | |
| 6,532,276 B1 | 3/2003 | Hartick et al. | |
| 6,542,574 B2 | 4/2003 | Grodzins | |
| 6,542,578 B2 | 4/2003 | Ries et al. | |
| 6,542,580 B1 | 4/2003 | Carver et al. | |
| 6,546,072 B1 | 4/2003 | Chalmers | |
| 6,552,346 B2 | 4/2003 | Verbinski et al. | |
| 6,563,903 B2 | 5/2003 | Kang et al. | |
| 6,580,778 B2 | 6/2003 | Meder | |
| 6,584,170 B2 | 6/2003 | Aust et al. | |
| 6,597,760 B2 | 7/2003 | Beneke et al. | |
| 6,606,516 B2 | 8/2003 | Levine | |
| 6,636,581 B2 | 10/2003 | Sorenson | |
| 6,653,588 B1 | 11/2003 | Gillard-Hickman | |
| 6,658,087 B2 | 12/2003 | Chalmers et al. | |
| 6,663,280 B2 | 12/2003 | Doenges | |
| 6,665,373 B1 | 12/2003 | Kotowski et al. | |
| 6,665,433 B2 | 12/2003 | Roder | |
| 6,812,426 B1 | 11/2004 | Kotowski et al. | |
| 6,816,571 B2 | 11/2004 | Bijjani et al. | |
| 6,837,422 B1 | 1/2005 | Meder | |
| 6,839,403 B1 | 1/2005 | Kotowski et al. | |
| 7,207,713 B2 | 4/2007 | Lowman | |
| 7,322,745 B2 | 1/2008 | Agrawal et al. | |
| 7,369,643 B2 | 5/2008 | Kotowski et al. | |
| 7,526,064 B2 * | 4/2009 | Akery | 378/57 |
| 2004/0141584 A1 | 7/2004 | Bernardi et al. | |

\* cited by examiner

MULTIPLE PASS CARGO INSPECTION SYSTEM

CROSS-REFERENCE TO RELATED APPLICATIONS

The present specification is a continuation of application Ser. No. 12/404,913, filed Mar. 16, 2009, now U.S. Pat. No. 7,860,213, which is a continuation of application Ser. No. 11/744,411, filed May 4, 2007, now U.S. Pat. No. 7,526,064, which claims priority from U.S. Provisional Application No. 60/746,540, filed on May 5, 2006.

FIELD OF THE INVENTION

The present invention relates generally to a system and method for inspecting cargo, and more specifically, to improved methods and systems for detecting materials concealed within a wide variety of receptacles, vehicles, and/or cargo containers. In particular, the present invention relates to improved systems and methods for inspecting a wide range of cargo sizes via a multiple pass, compact inspection system while maintaining optimal overall inspection throughput.

BACKGROUND OF THE INVENTION

Trade fraud, smuggling, and terrorism have increased the need for non-intrusive inspection systems such as X-ray, gamma ray and linear accelerator (LINAC)-based systems for inspecting cargo, trucks, passenger vehicles, and other transportation systems, which efficiently provide for the movement of commodities across borders. In addition, they provide opportunities for the inclusion of contraband items such as weapons, explosives, illicit drugs and precious metals. In particular, non-intrusive inspection systems are used in applications ranging from curbside inspection of parked vehicles to scanning in congested or high traffic ports. The term port, while generally accepted as referring to a seaport, also applies to a land border crossing or any port of entry.

The size of the cargo or vehicle under inspection generally determines the size of the imaging system and thus, in general the bigger the object under inspection, the bigger the inspection system.

With an increase in global commerce, port authorities require additional sea berths and associated container storage space. Additional space requirements are typically met by the introduction of higher container stacks, an expansion of ports along the coastline, or by moving inland. However, these scenarios are not typically feasible. Space is generally in substantial demand and short supply. Existing ports operate under a routine that is not easily modified without causing disruption to the entire infrastructure of the port. The introduction of new procedures or technologies often requires a substantial change in existing port operating procedures in order to contribute to the port's throughput, efficiency, and operability.

With limited space available and a need to expand for increased inspection performance, finding suitable space to accommodate additional inspection facilities along the normal process route remains difficult. Moreover, systems incorporating the high energy X-ray sources, or linear accelerators (LINAC), require either a major investment in shielding material (generally in the form of concrete formations or buildings) or the use of exclusion zones (dead space) around the building itself. In either case, the building footprint is significant depending upon the size of cargo containers to be inspected. Thus, the continual conflict is between making the system as small as possible while capable of inspecting a varying range of objects, including large objects.

A typical size range for objects under inspection includes vehicles as small as compact automobiles (or even smaller) to trucks carrying large containers. Thus, the object under inspection typically ranges from a compact automobile as small as 1.2 meters wide by 1.2 meters high to a large truck that is up to 3 meters wide and 4.6 meters high.

Therefore, there is a need for a relatively compact inspection system that produces at least one image of objects of varying sizes. What is also needed is a relatively compact inspection system that is capable of producing an image of an object in a single, first-pass image scan with no corner cut-off for smaller vehicles.

What is also needed is a relatively compact inspection system that is capable of producing an image of a large object in a multiple pass image scan in situations where a first pass image scan does not produce an image of a large object under inspection without corner cut off.

What is also needed is a relatively compact multiple pass inspection system that maintains overall inspection throughput.

SUMMARY OF THE INVENTION

The present invention is a cargo inspection system, employing a radiation source, capable of scanning vehicles and/or cargo in a wide range of sizes, including conventional imaging areas as well as taller and bulkier enclosures at sufficiently optimal efficacy and overall throughput. In one embodiment, the present invention is a multiple pass inspection method for inspecting vehicles and their cargo, comprising a first pass scan, wherein said first pass scan includes moving a radiation source at a suitable scanning distance, rotating a radiation source at a suitable scanning angle, and moving said radiation source along an object under inspection.

The multiple pass inspection system for inspecting vehicles and their cargo comprises a radiation source having translational and rotational movement, a detector array having rotational movement, and a movable gantry. Optionally, the detector array is rotated about an axis at an angle equal to that of the radiation source, so that they are in continual alignment. Optionally, the multiple pass inspection system of claim 4 wherein the radiation source and the detector array are mounted on the movable gantry.

In another embodiment, the present invention is a multiple pass inspection method for inspecting vehicles and their cargo, comprising at least a first pass scan and a second pass scan, wherein said first pass scan includes moving a radiation source at a first suitable scanning distance, rotating a radiation source at a first suitable scanning angle, and moving said radiation source along an object under inspection and wherein said second pass scan includes moving a radiation source at a second suitable scanning distance, rotating a radiation source at a second suitable scanning angle, and moving said radiation source along an object under inspection.

In another embodiment, the present invention is a multiple pass inspection method for inspecting vehicles and their cargo, comprising at least a first pass scan, a second pass scan, and a third pass scan, wherein said first pass scan includes moving a radiation source at a first suitable scanning distance, rotating a radiation source at a first suitable scanning angle, and moving said radiation source along an object under inspection; wherein said second pass scan includes moving a radiation source at a second suitable scanning distance, rotating a radiation source at a second suitable scanning angle, and moving said radiation source along an object under inspection; and wherein said third pass scan includes moving a radiation source at a third suitable scanning distance, rotating a radiation source at a third suitable scanning angle, and moving said radiation source along an object under inspection.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

Figure 1:
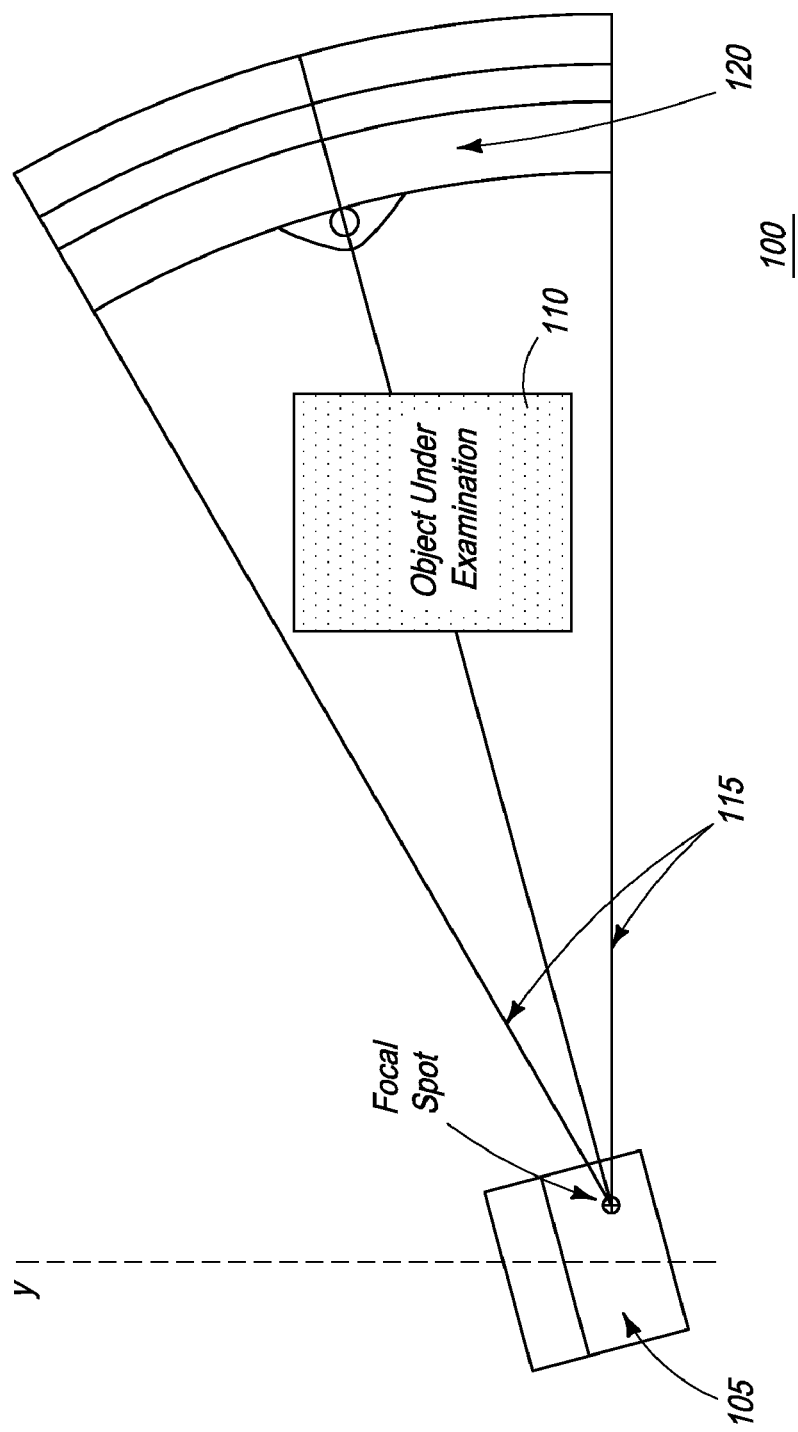
FIG. 1 is side perspective view of one embodiment of the multiple pass inspection system of the present invention in a single pass use configuration, illustrating the radiation beam and scan area.

The present invention is directed toward a system and method for inspecting cargo, and more specifically, to improved methods and systems for detecting materials concealed within a wide variety of receptacles, vehicles, and/or cargo containers. In particular, the present invention is directed towards improved systems and methods for inspecting a wide range of cargo sizes via a multiple pass, compact inspection system while maintaining optimal overall inspection throughput.

Reference will now be made to specific embodiments of the present invention. The embodiment described herein is not a general disavowal of any one specific embodiment or used to limit the claims beyond the meaning of the terms used therein.

In one embodiment, the present invention is a multiple pass cargo inspection system, employing a radiation source, capable of scanning vehicles and/or cargo in a wide range of sizes, including conventional imaging areas as well as taller and bulkier enclosures at sufficiently optimal efficacy and overall throughput. In one embodiment, the radiation source is an X-ray source. In another embodiment, the radiation source is a gamma ray source. In yet another embodiment, the radiation source is a linear accelerator (LINAC).

In one embodiment, the multiple pass inspection system of the present invention comprises a radiation source and detector array that can arranged and/or situated in various positions for scanning an object under inspection. In one embodiment, the radiation source is capable of translational movement along a y-axis in a three-dimensional coordinate system wherein the x-axis represents horizontal movement, the y-axis represents vertical movement, and the z-axis represents rotational movement. In another embodiment, the source is positioned on the y-axis and pivoted about the z-axis for optimal translational and rotational movement, respectively. Thus, the radiation source can be raised or lowered vertically and/or tilted or spun about an axis.

In one embodiment, the detector array employed in the multiple pass cargo inspection system of the present invention can be rotated about an axis in the same fashion as the radiation source. In one embodiment, the detector array is rotated at an angle equal to that of the radiation source, so that they are in continual alignment.

In one embodiment, the radiation source and detector package are mounted on a conventional gantry transport system such that both source and detector array can be moved across the length of the inspection area.

In one embodiment of the multiple pass inspection system of the present invention, the inspection system operates and scans an entire object under inspection in a single pass. In this configuration, the gantry transport system moves the radiation source once across the length of the inspection area, thereby illuminating the inspection area with a diverging fan beam of radiation.

In one embodiment, the inspection system operates and scans the object under inspection in a plurality of passes. Thus, the multiple pass cargo inspection system is capable of scanning objects of all sizes, including vehicles and tall and/or bulky objects. In one embodiment, the inspection system is a dual pass scanning system. In a first pass, the radiation source and detector array are vertically positioned and tilted in a first position to scan a lower portion of the inspection area and thus, object under inspection. In a second pass, the radiation source and detector array are vertically positioned and tilted in a second position to scan an upper portion of the inspection area, and thus, object under inspection.

For example, during a first pass, the radiation source and detector array are placed at a lower position, or at a lower point on the y-axis of the inspection system. The gantry system is then moved forward to travel across the distance of the length of the inspection area, and scans the lower portion of the inspection area. Upon reaching the end of the length of the inspection area, the radiation source and detector array are re-positioned to an upper scanning position, or at a higher point on the y-axis of the inspection system. During a second pass, the gantry system is moved backward to travel in a reverse direction across the distance of the length of the inspection area, and scans the upper portion of the inspection area.

In another embodiment, the inspection system is a triple pass scanning system. The first and second pass scanning methods have been described above and are herein incorporated by reference. In one embodiment, in the third pass scan, the radiation source and detector array are placed in a central position on the vertical y-axis. The third pass scan is usually initiated in situations where the first pass and second pass scan are not sufficient to completely scan a tall or bulky object under inspection.

Optionally, when at the appropriate y-axis positions, the source can be tilted or rotated about the z-axis.

In one embodiment, the third pass scan allows for multiple views at different angles of an inspection area in which a threat item is otherwise obscured in a first pass scan or second pass scan. In one exemplary scanning sequence, once the lower portion of the inspection area has been scanned with the radiation source in a forward direction, the radiation source is vertically and angularly positioned to the central point of the y-axis. The gantry is then moved in a reverse direction back to the starting point of inspection, thus scanning the mid-region of the inspection area. The source is then moved to a higher vertical position while at the start of the inspection area and moved in a forward direction through the inspection area, resulting in a scan image of the upper portion of the inspection area.

It should be understood by those of ordinary skill in the art that in a dual pass scan, scanning can begin from any vertical position and at any tilt of the radiation source and detector array. In one embodiment, to maximize the overall throughput of the system, a second complete scan of a second object under inspection can begin from the last position in which the source was at the completion of scanning for a first object under inspection. Each successive scan of an object under inspection can also begin with the radiation source in its last scan position from the previous object under inspection.

In addition, it should be understood by those of ordinary skill in the art that in a triple pass scan, the scanning sequence can be customized by an operator depending upon the size of the inspection area and/or the last scan position of the radiation source from the previous object under inspection, while still maintaining high throughput of the inspection system.

FIG. 1 is side perspective view of one embodiment of the multiple pass inspection system of the present invention in a single pass use configuration, illustrating the radiation beam and scan area. In one embodiment, multiple pass inspection system 100 comprises a radiation source 105, for irradiating an object under inspection 110 with a vertically divergent fan beam of radiation 115.

Radiation source 105 may be, but is not limited to, an X-ray source, a linear accelerator (LINAC), or a gamma radiation source. Preferably, the radiation source 105 includes a radio-isotopic source, an X-ray tube or any other source known in the art capable of producing beam flux and energy sufficiently high to direct a beam to traverse the space through an object under inspection to detectors at the other side. The choice of source type and its intensity and energy depends upon the sensitivity of the detectors, the radiographic density of the cargo in the space between the source and detectors, radiation safety considerations, and operational requirements, such as the inspection speed. One of ordinary skill in the art would appreciate how to select a radiation source type, depending upon his or her inspection requirements. In one embodiment, where the object under inspection is a large sized container or car that highly attenuates the X-ray beam, the radiation could be from an X-ray tube operating at a voltage in substantial excess of 200 keV, and may operate in a region of approximately 4.5 MeV and even up to 10 MeV or more.

In one embodiment, object under inspection 110 is a vehicle, truck, or other container for carrying cargo or passenger luggage or general belongings.

Multiple pass inspection system 100 further comprises detector array 120, which is preferably positioned behind object under inspection 110 and is used to detect radiation transmitted through the object under inspection 110. The detectors may be formed by a stack of crystals that generate analog signals when X-rays impinge upon them, with the signal strength proportional to the amount of beam attenuation in the object under inspection 110. In one embodiment, the X-ray beam detector arrangement consists of a linear array of solid-state detectors of the crystal-diode type. A typical arrangement uses cadmium tungstate scintillating crystals to absorb the X-rays transmitted through the object under inspection and to convert the absorbed X-rays into photons of visible light. Crystals such as bismuth germinate, sodium iodide or other suitable crystals may be alternatively used as known to a person of ordinary skill in the art. The crystals can be directly coupled to a suitable detector, such as a photodiode or photo-multiplier. The detector photodiodes could be linearly arranged, which through unity-gain devices, provide advantages over photo-multipliers in terms of operating range, linearity and detector-to-detector matching. In another embodiment, an area detector is used as an alternative to linear array detectors. Such an area detector could be a scintillating strip, such as cesium iodide or other materials known in the art, viewed by a suitable camera or optically coupled to a charge-coupled device (CCD).

As described above, during inspection, inspection system 100, and more specifically radiation source 105 and detector array 120, is moved horizontally across the length of the inspection area of inspection system 100 such that the vertically extending fan beam 115 scans slices of the object under inspection 110 across its overall length. Thus, multiple pass inspection system 100 is preferably mounted on a gantry type transport system, as shown in FIG. 2, to allow for vertical, horizontal, and rotational movement of both the radiation source 105 and detector array 120.

Figure 2:
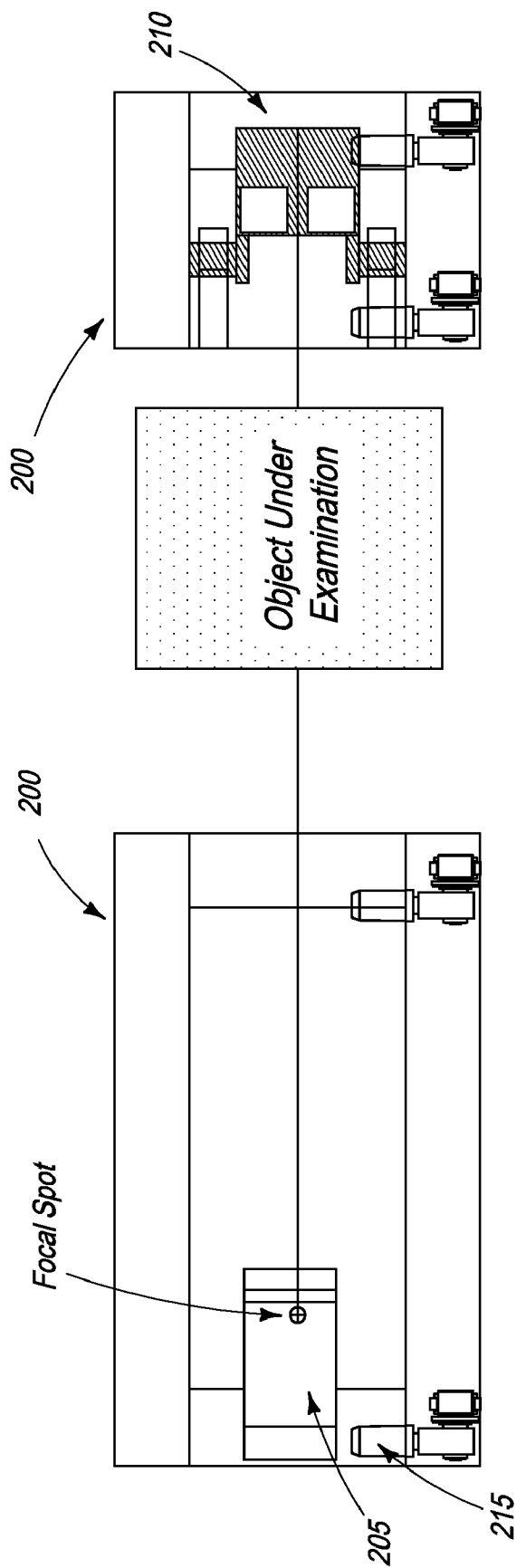
FIG. 2 is a top perspective view of one embodiment of the multiple pass inspection system of the present invention, further depicting a typical gantry transport system.

Now referring to FIG. 2, a top perspective view of one embodiment of the multiple pass inspection system of the present invention is shown, further depicting a typical gantry transport system 200, as described with respect to FIG. 1. Typical gantry-type transport systems are well-known to those of ordinary skill in the art and thus will not be described in detail herein. In one embodiment, the radiation source 205 and detector array 210 are mounted on a gantry transport system 200 such that both source and detector array can be moved across the length (x-axis) of the inspection area in translational movement. In another embodiment, as described in further detail with respect to FIGS. 3a and 3b, the radiation source and detector array are mounted on a gantry transport system 200 such that both source and detector array can be moved in a vertical direction (y-axis). In another embodiment, also as described in further detail with respect to FIGS. 3a and 3b, the radiation source and detector array are mounted on a gantry transport system 200 such that both source and detector array can be moved in a rotational direction (z-axis).

In one embodiment, radiation source 205 is located on the gantry transport system and attached such that it is capable of both translational and rotational movement. In one embodiment, radiation source 205 is vertically displaced using a screw jack mechanism 215. Screw jack mechanisms are well-known to those of ordinary skill in the art and their operation will not be described herein. It should be noted, however, that the radiation source 205 is both raised and lowered using the screw jack mechanism 215. In one embodiment, radiation source 205 is positioned on a rotatable platform boom (not shown), allowing for rotational movement in a range of 0 to 90 degrees.

Referring back to FIG. 1, the radiation transmitted through the object under inspection 110 is attenuated to varying degrees by the object under inspection and its contents. The attenuation of the radiation is a function of the density and atomic composition of the materials through which the radiation passes. The attenuated radiation is detected and radiographic images of the contents of the object under inspection 110 are generated. In one embodiment, the resultant images show the shape, size and varying densities of the contents.

Standard cargo containers are typically 20-50 feet long (6.1-15.2 meters), 8-10 feet high (2.4-3.0 meters) and 6-8 feet wide (1.8-2.4 meters). Air cargo containers and Unit Load Devices (ULDs), which are used to contain a plurality of pieces of luggage or other cargo to be stored in the body of an airplane, may range in size (length, height, width) from about 35×21×21 inches (0.89×0.53×0.53 meters) up to about 240× 118×96 1 inches (6.1×3.0×2.4 meters). Sea cargo containers are typically about 40 feet long, 8 feet wide and 8 feet high.

In conventional inspection systems, to illuminate an object under inspection uniformly with an X-ray fan beam, the radiation source is placed at a distance relatively far from the object under inspection. For example, but not limited to such example, to illuminate a cargo container with a height of about 8 feet (2.4 meters) with a vertical radiation beam emitted over an angle of about 24 degrees (+/−12 degrees from the central ray), the source should be about 19 feet (about 5.8 meters) from the face of the cargo container. If the beam is emitted over an angle of about 120 degrees (+/−60 degrees from the central ray), however, the source may be placed about 2.5 feet (about 0.8 meters) from the face of the cargo container.

The multiple pass inspection system 100 of the present invention, however, is more compact and allows for the radiation source to be placed closer to the object under inspection than with current systems. Thus, multiple pass inspection system 100 is compact and space-saving, and minimizes the probability of a decline in radiation intensity due to the distance between the radiation source and the object under inspection.

Because the multiple pass inspection system 100 is compact, it is capable of producing an image of an object under inspection of in a width of up to 3 meters and a height of up to 2 meters in a single image scan. In a single pass scan configuration, the gantry transport system is moved once across the length of the object under inspection. The angle of the fan beam is sufficient to illuminate the entire face of the object under inspection 110. This single image scan, or first pass scan, provides an image with no 'corner cut-off' for all passenger cars, small vans and buses, and for a typical check point is suitable for at least 90% of total throughput.

When object under inspection is larger than a passenger vehicle, however, the single, first pass scan is only capable of producing an image of a lower portion of the object under inspection. Thus, a plurality of passes is required to fully illuminate and scan objects under inspection that are taller than a typical height of 2 meters.

Figure 3A:
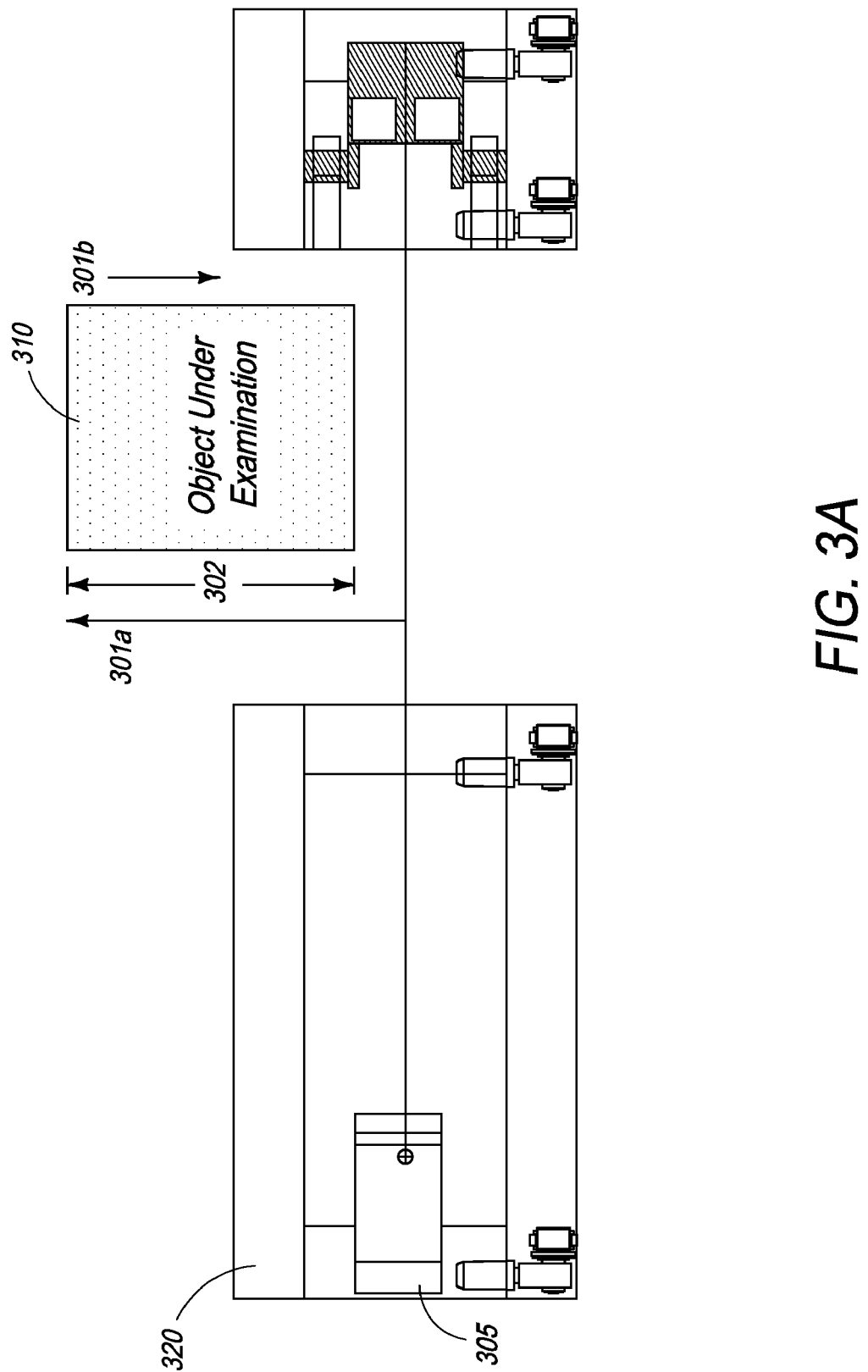
FIG. 3a is a top perspective view of one embodiment of the multiple pass inspection system of the present invention, in a dual pass configuration, further illustrating the scanning directions.
Figure 3B:
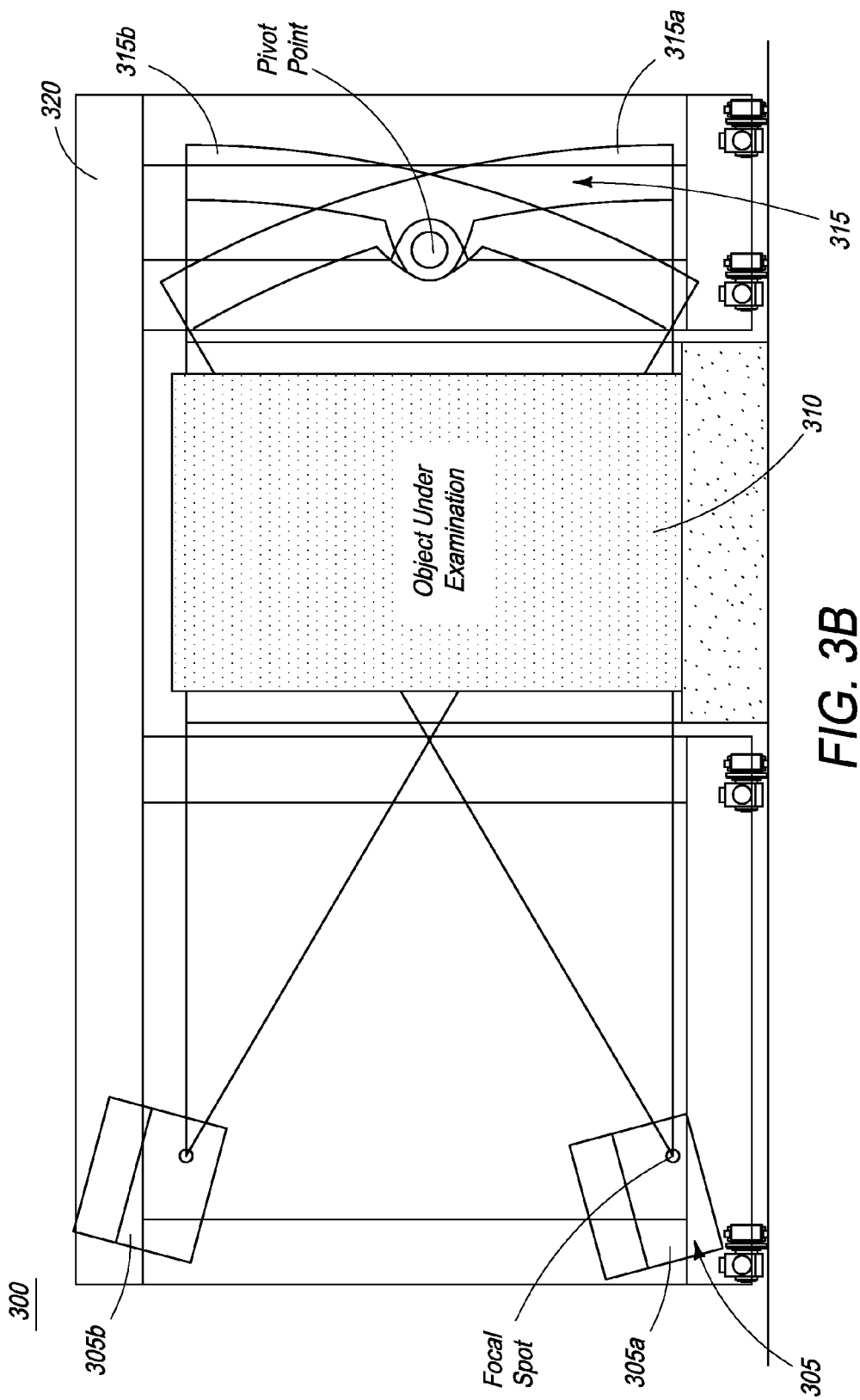
FIG. 3b is a side perspective view of one embodiment of the multiple pass inspection system of the present invention, in a dual pass configuration, further illustrating the radiation beam and scan area.

FIG. 3a is a top perspective view of one embodiment of the multiple pass inspection system of the present invention, in a dual pass configuration, further illustrating the scanning directions. FIG. 3b is a side perspective view of one embodiment of the multiple pass inspection system of the present invention, in a dual pass configuration, further illustrating the radiation beam and scan area.

Referring now to both FIGS. 3a and 3b, multiple pass inspection system 300 employs a dual pass scan to completely irradiate and scan a large object under inspection 310. In operation, at the start of the inspection process, the radiation source 305 has a first vertical position (not shown) and a first angular position 305a such that it illuminates the lower portion of the object under inspection 310. Referring now to both FIGS. 3a and 3b, as gantry transport system 320 moves horizontally in a first pass scan direction 301a across length 302 of the object under inspection 310, the radiation transmitted through the lower portion of the object under inspection 310 is detected by the detector array 315 placed at a corresponding first angular position 315a so that it is in alignment with the radiation source 305 placed at a first angular position 305a.

On reaching the end of the length 302 of the object under inspection 310, the source 305 is raised to a second vertical position (not shown) and a second angular position 305b. Correspondingly, the detector array 315 is moved into a second angular position 315b so that it is in alignment with the radiation source 305 placed at a second angular position 305b. Thereafter, the gantry transport system 320 moves horizontally, in a second pass scan reverse direction 301b, and reaches the inspection starting point while in the process scanning the upper portion of the object under inspection 310. Thus, by using the gantry's return trip to perform a second scan, scanning time is minimized and system throughput is enhanced.

Where a 'first pass' scan in the forward direction is sufficient to image the full height of the object, the reverse direction or return trip scan is used for the subsequent vehicle under inspection thus eliminating the need to move the scanner back to the original start position and maximizing the system throughput.

Figure 4:
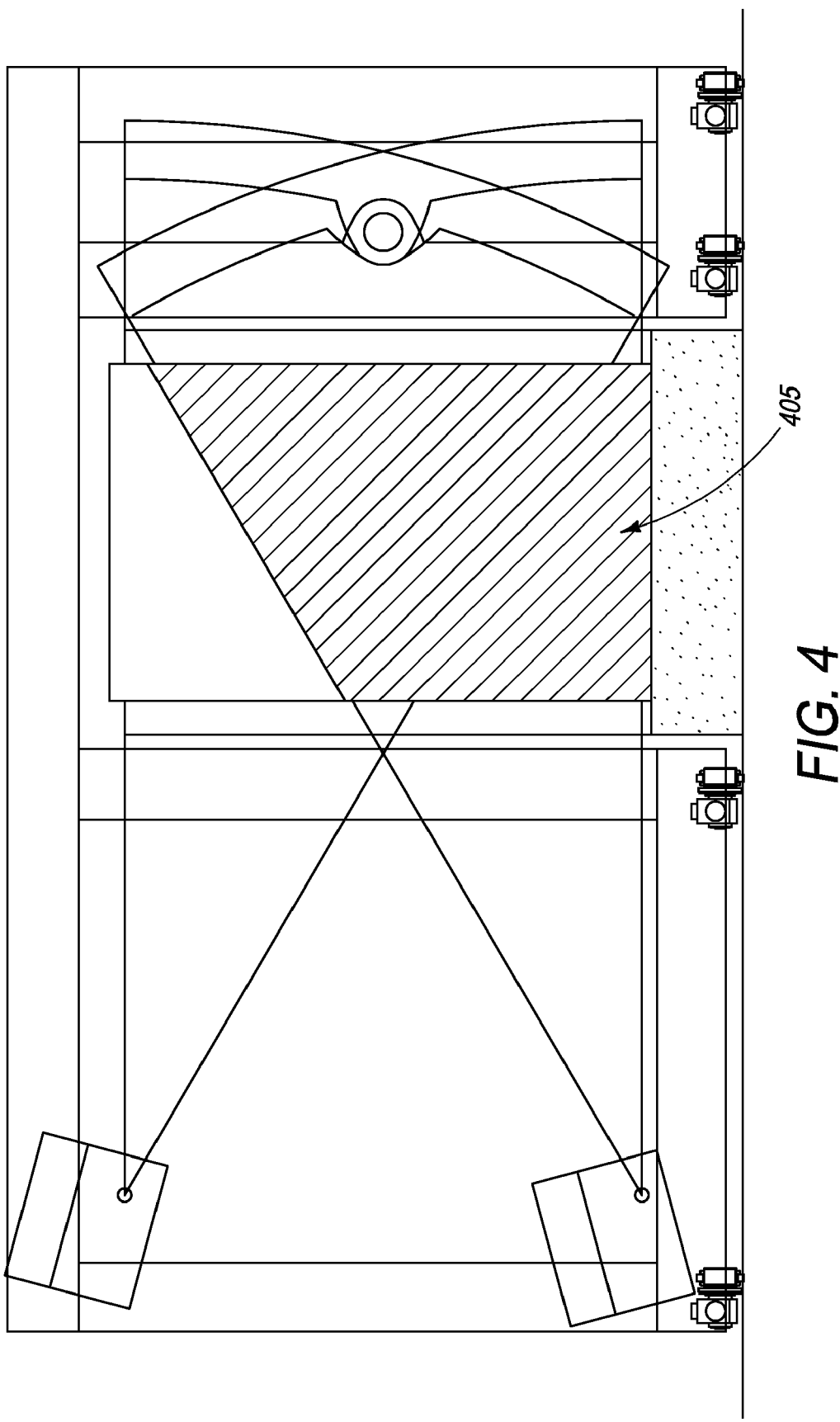
FIG. 4 is a depiction of the imaging area in one embodiment of the multiple pass cargo inspection system of the present invention, illustrating the imaging area resulting from a first pass lower position scan in a multiple pass configuration.

FIG. 4 is a depiction of the imaging area in one embodiment of the multiple pass cargo inspection system of the present invention, illustrating the imaging area resulting from a first pass lower position scan in a multiple pass configuration. As shown in FIG. 4, after a first pass lower position scan of an object under inspection, imaging area 405 is obtained.

Figure 5:
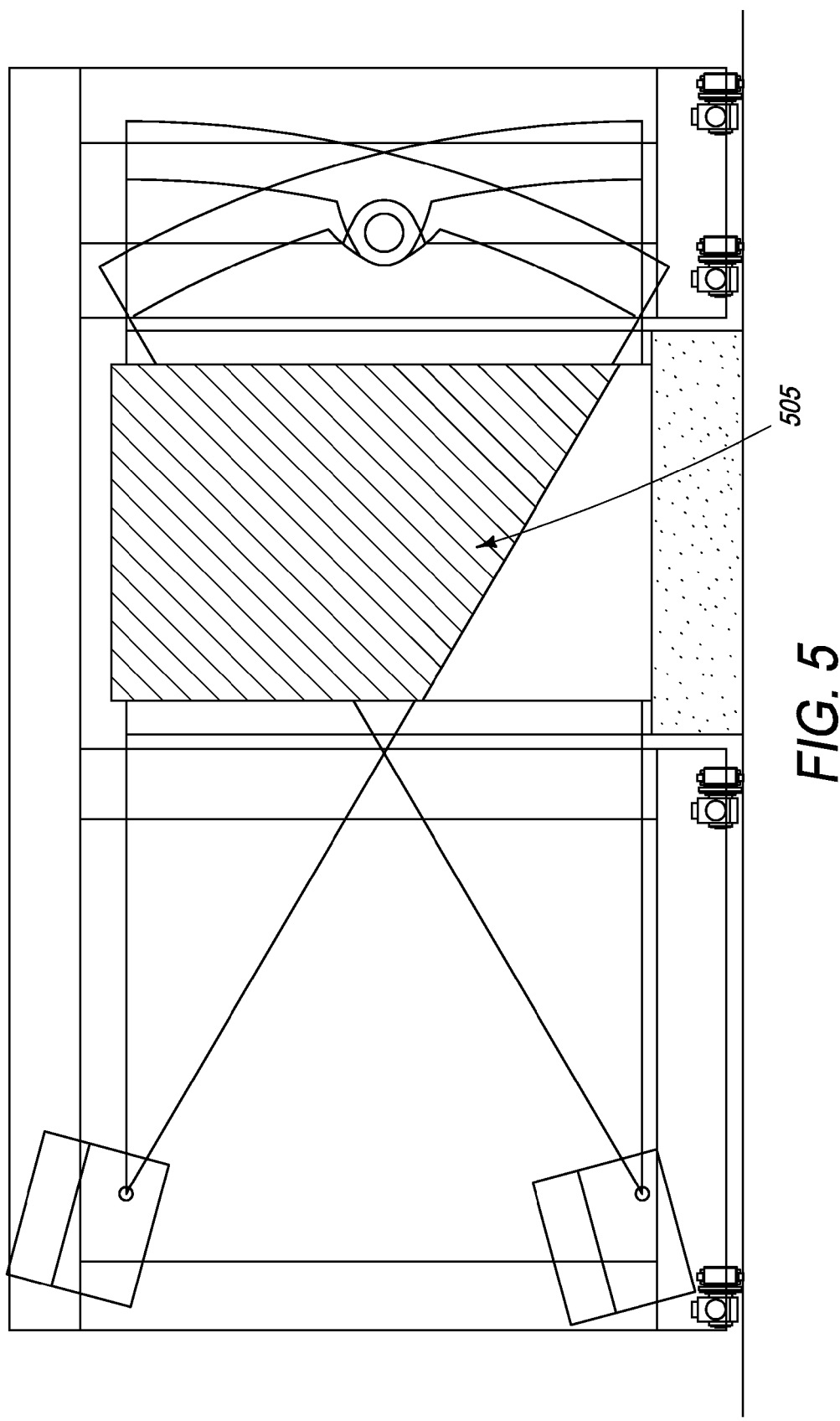
FIG. 5 is a depiction of the imaging area in one embodiment of the multiple pass cargo inspection system of the present invention, illustrating the imaging area resulting from a second pass upper position scan in a multiple pass configuration.

FIG. 5 is a depiction of the imaging area in one embodiment of the multiple pass cargo inspection system of the present invention, illustrating the imaging area resulting from a second pass upper position scan in a multiple pass configuration. As shown in FIG. 4, after a second pass upper position scan of an object under inspection, imaging area 505 is obtained.

Figure 6:
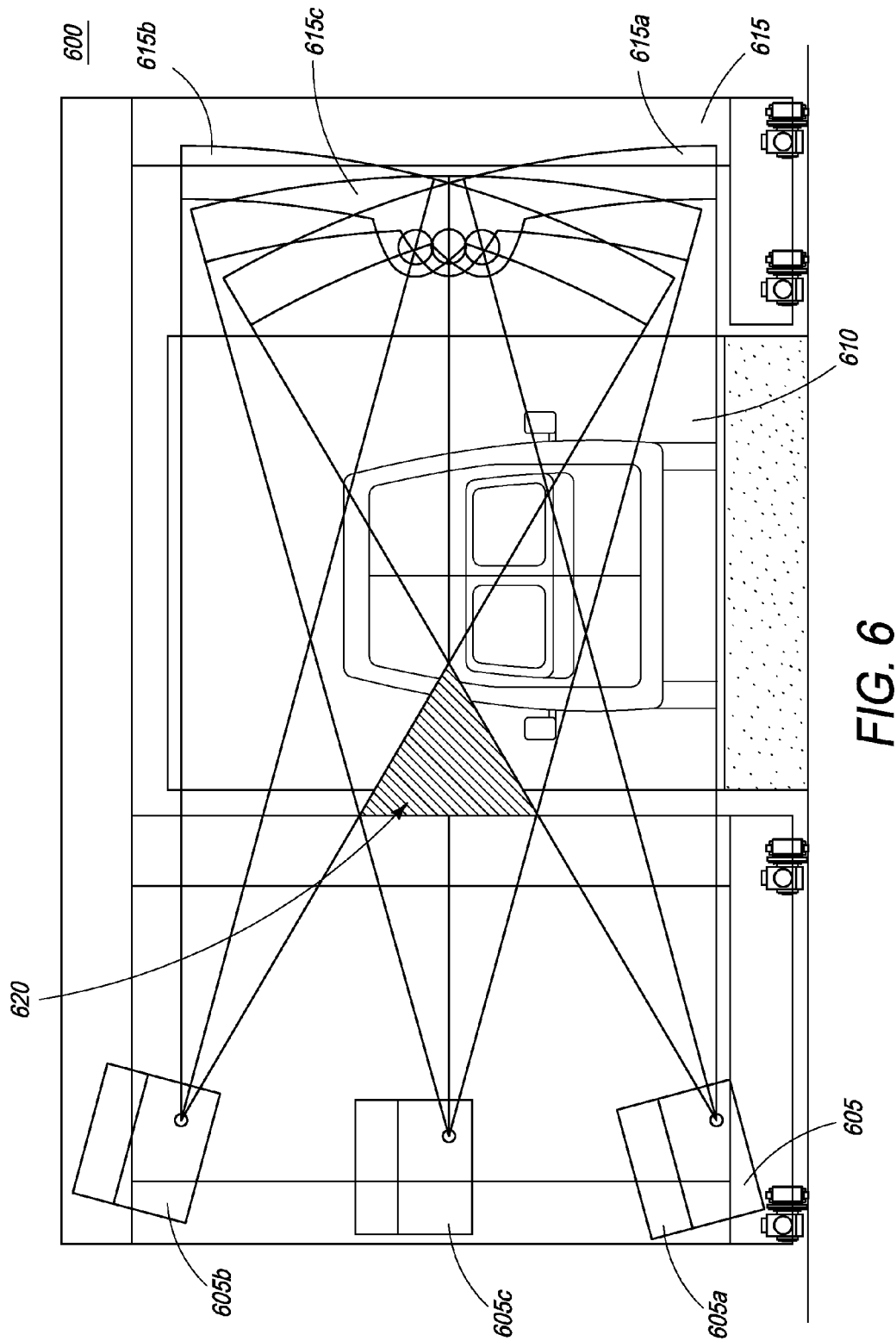
FIG. 6 is a depiction of the imaging area in one embodiment of the multiple pass cargo inspection system of the present invention, illustrating the imaging area resulting from a third pass central position scan in a multiple pass configuration.

FIG. 6 is a depiction of the imaging area in one embodiment of the multiple pass cargo inspection system of the present invention, illustrating the imaging area resulting from a third pass central position scan in a multiple pass configuration. Thus, in situations where a dual pass scan is not sufficient to completely scan the object under inspection, it is possible to vertically position the radiation source at varying heights to provide additional scans covering different parts of the object under inspection.

As shown in FIG. 6, three passes are employed to completely scan a large object under inspection. Lower and upper scan positions 605a and 605b and corresponding lower and upper detector positions 615a and 615b, are not sufficient to completely cover the entire volume of the object under inspection 610 (and effectively, the entire inspection volume or area) and thus, leaves volume 620 not inspected. Thus, in order to scan volume 620, the source is positioned at a central point 605c on the vertical axis and detector array 615 is positioned at corresponding position 615c. This central radiation source point scanning feature also allows multiple views at differing angles of the object under inspection, which in certain circumstances may help reveal a threat item otherwise obscured in the image in a single or a dual image scan.

In operation of the triple pass inspection system, after the source has scanned the object under inspection by moving forward along the x-axis and in the lower position, the source is vertically and angularly positioned at a central point and is then moved in the reverse direction back to the starting point, scanning the central region of the object under inspection. The source is then moved in the upper position, and translated in the forward direction along the x-axis, scanning the upper portion of the object under inspection.

Figure 7:
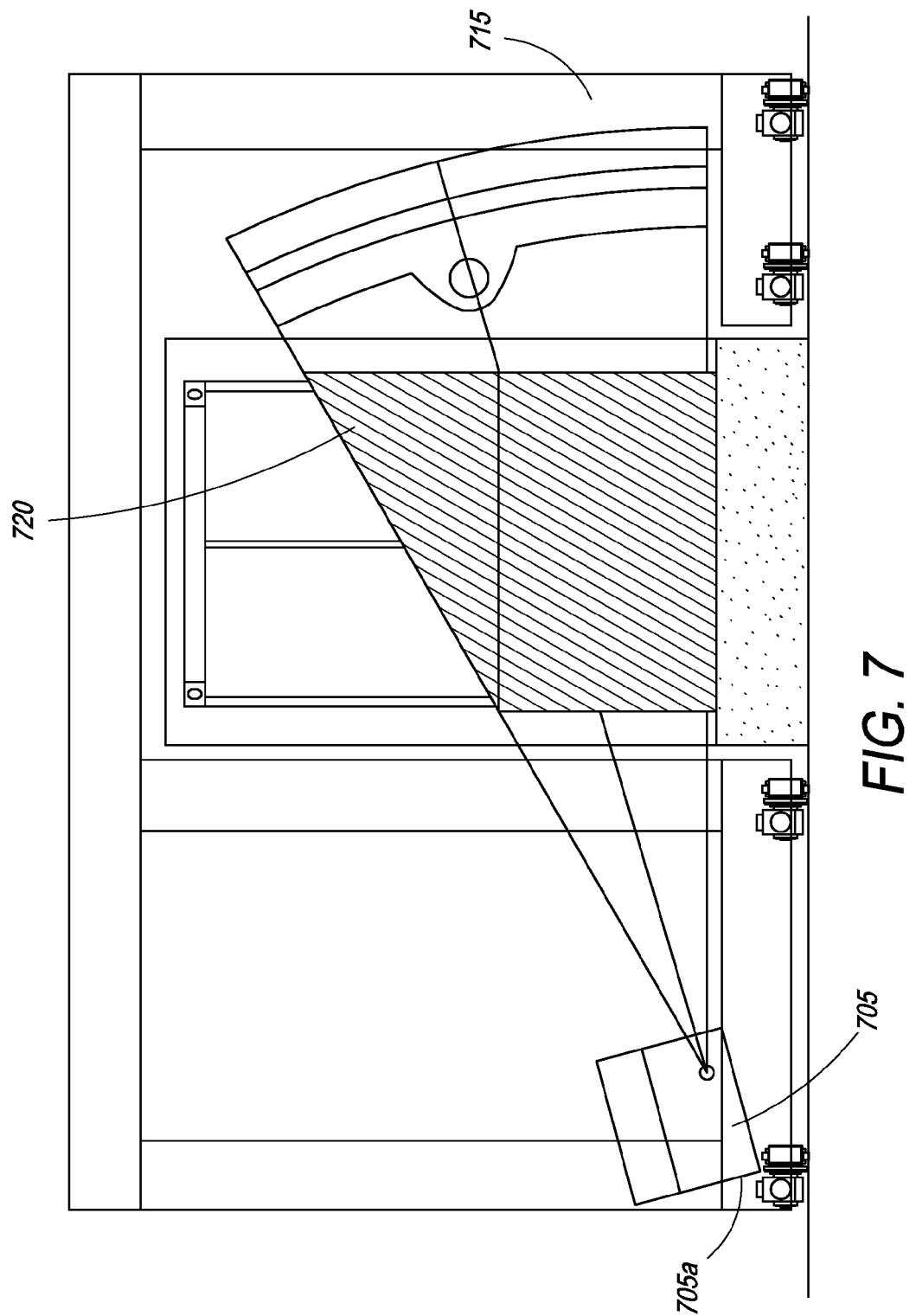
FIG. 7 is a depiction of the imaging area in one embodiment of the multiple pass cargo inspection system of the present invention, illustrating the imaging area resulting from a first pass lower position scan in a triple pass configuration, while inspecting a large truck.

FIG. 7 is a depiction of the imaging area in one embodiment of the multiple pass cargo inspection system of the present invention, illustrating the imaging area resulting from a first pass lower position scan in a triple pass configuration, while inspecting a large truck. In one embodiment, radiation source 705 is placed at a first position 705a on the gantry, lower on the y-axis. In addition, detector array 715 is placed at a first position 715a, so that the radiation source 705 and detector array 715 are in alignment. Once the scan of the object under inspection, or large truck, is complete, lower imaging area 720 is obtained.

Figure 8:
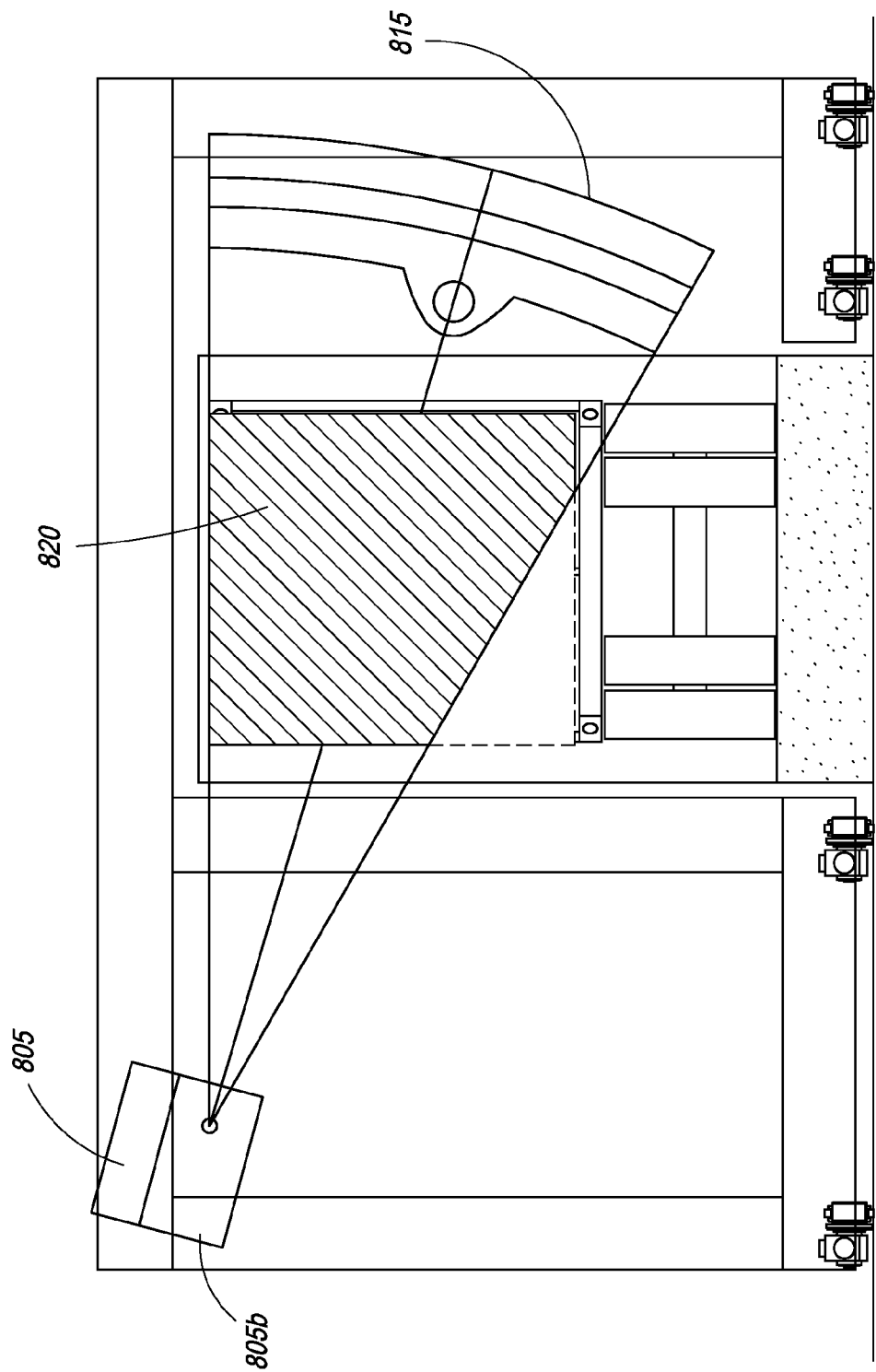
FIG. 8 is a depiction of the imaging area in one embodiment of the multiple pass cargo inspection system of the present invention, illustrating the imaging area resulting from a second pass upper position scan in a triple pass configuration, while inspecting a large truck.

FIG. 8 is a depiction of the imaging area in one embodiment of the multiple pass cargo inspection system of the present invention, illustrating the imaging area resulting from a second pass upper position scan in a triple pass configuration, while inspecting a large truck. In one embodiment, radiation source 805 is placed at a second position 805b on the gantry, lower on the y-axis. In addition, detector array 815 is placed at a second position 815b, so that the radiation source 805 and detector array 815 are in alignment. Once the scan of the object under inspection, or large truck, is complete, upper imaging area 820 is obtained.

Figure 9:
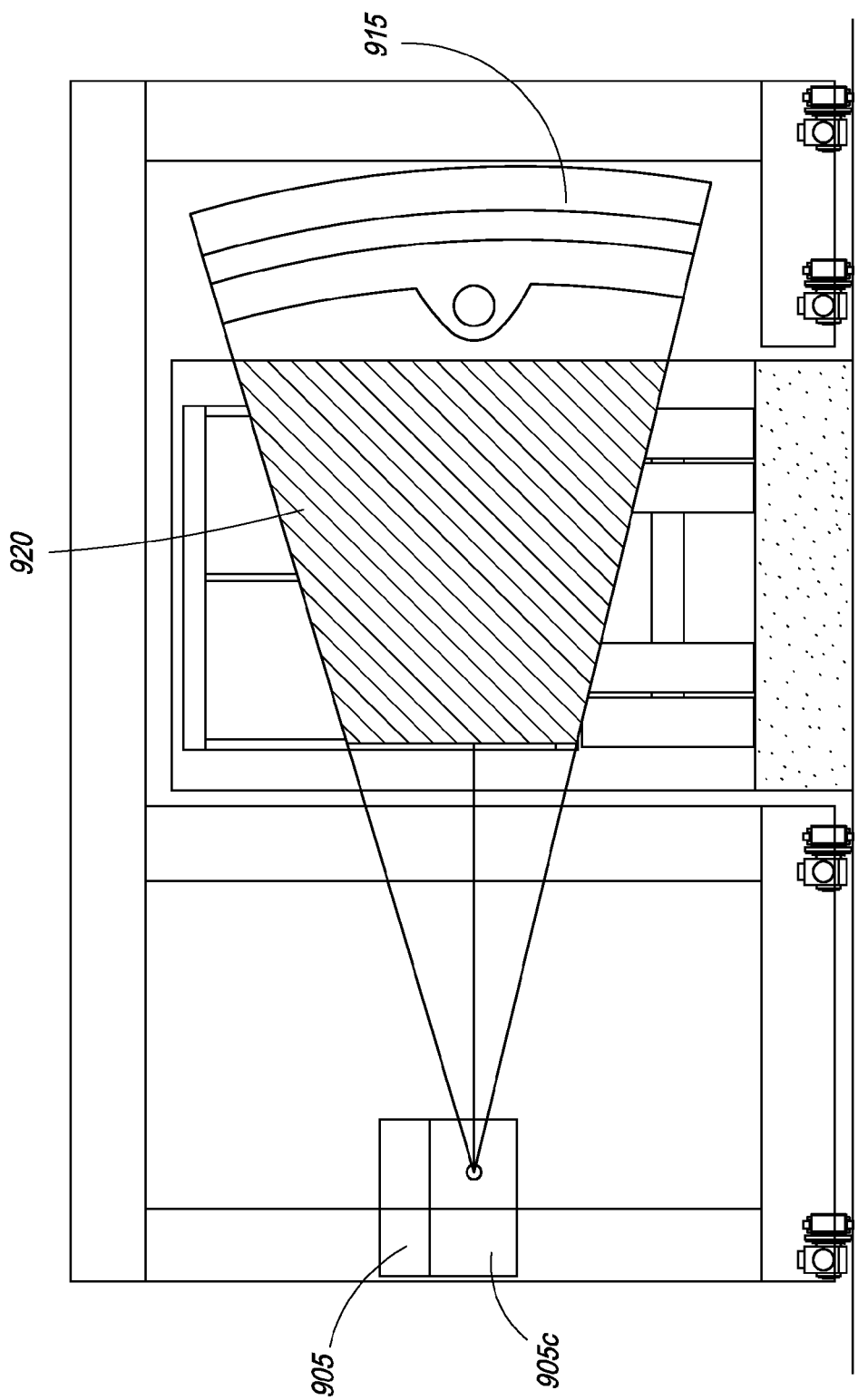
FIG. 9 is a depiction of the imaging area in one embodiment of the multiple pass cargo inspection system of the present invention, illustrating the imaging area resulting from illustrating the imaging area resulting from a third pass central position scan in a multiple pass configuration, while inspecting a large truck.

FIG. 9 is a depiction of the imaging area in one embodiment of the multiple pass cargo inspection system of the present invention, illustrating the imaging area resulting from illustrating the imaging area resulting from a third pass central position scan in a multiple pass configuration, while inspecting a large truck. In one embodiment, radiation source 905 is placed at a third position 805c on the gantry, at the central point on the y-axis. In addition, detector array 915 is placed at a second position 915b, so that the radiation source 905 and detector array 915 are in alignment. Once the scan of the object under inspection, or large truck, is complete, central imaging area 920 is obtained.

Thus, in one embodiment, in operation, the multiple pass cargo inspection system of the present invention may be varied to optimize the overall throughput of the scanning system, including but not limited to a change in scan sequence. For example, but not limited to such example, if an object under inspection is scanned using any of the multiple pass inspection methods, it is possible that at the end of the last pass the source is in the upper position on the y-axis as described above and ready to move forward on the x-axis. In this case, the subsequent object under inspection may be scanned beginning with the upper forward position, such that the gantry moves backward along the length of the object under inspection to scan the upper portion of the object under inspection first. Thereafter, depending upon the scanning requirement, the source can be positioned at other positions to completely scan the object under inspection. The invention, as described herein, is not limited to such scan sequences and it should be understood by those of ordinary skill in the art that any number of scan sequences are possible.

Figure 10:
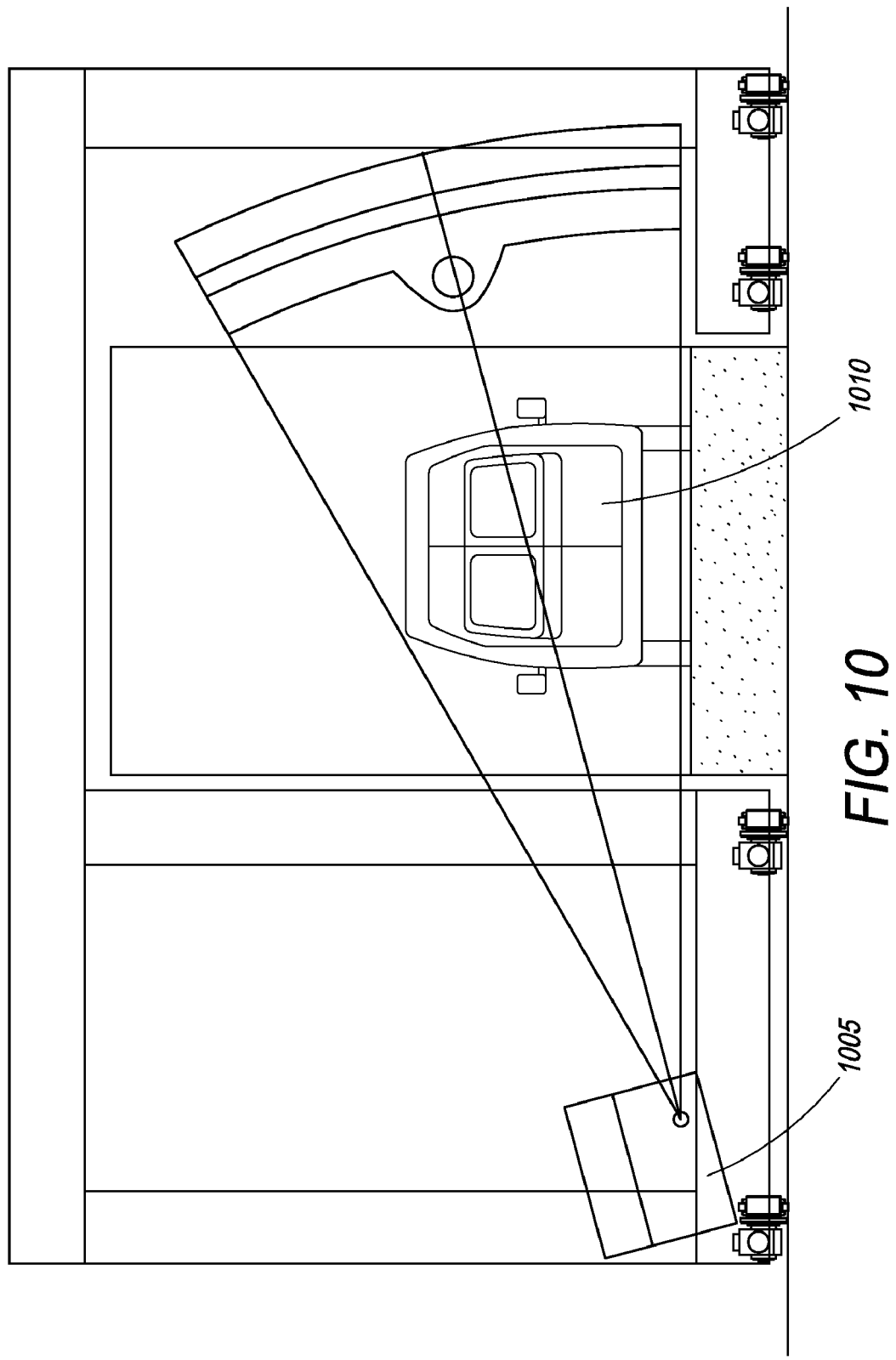
FIG. 10 illustrates one embodiment of the multiple pass inspection system of the present invention wherein the source may be vertically positioned to completely scan an object under inspection in a single pass.

FIG. 10 illustrates one embodiment of the multiple pass inspection system of the present invention wherein the source may be vertically positioned to completely scan an object under inspection in a single pass. If a single pass scan is sufficient to cover the entire volume of the object under inspection, the source 1005 can be vertically positioned at a point that is most favorable to allow for the coverage of the entire object under inspection 1010.

Figure 11:
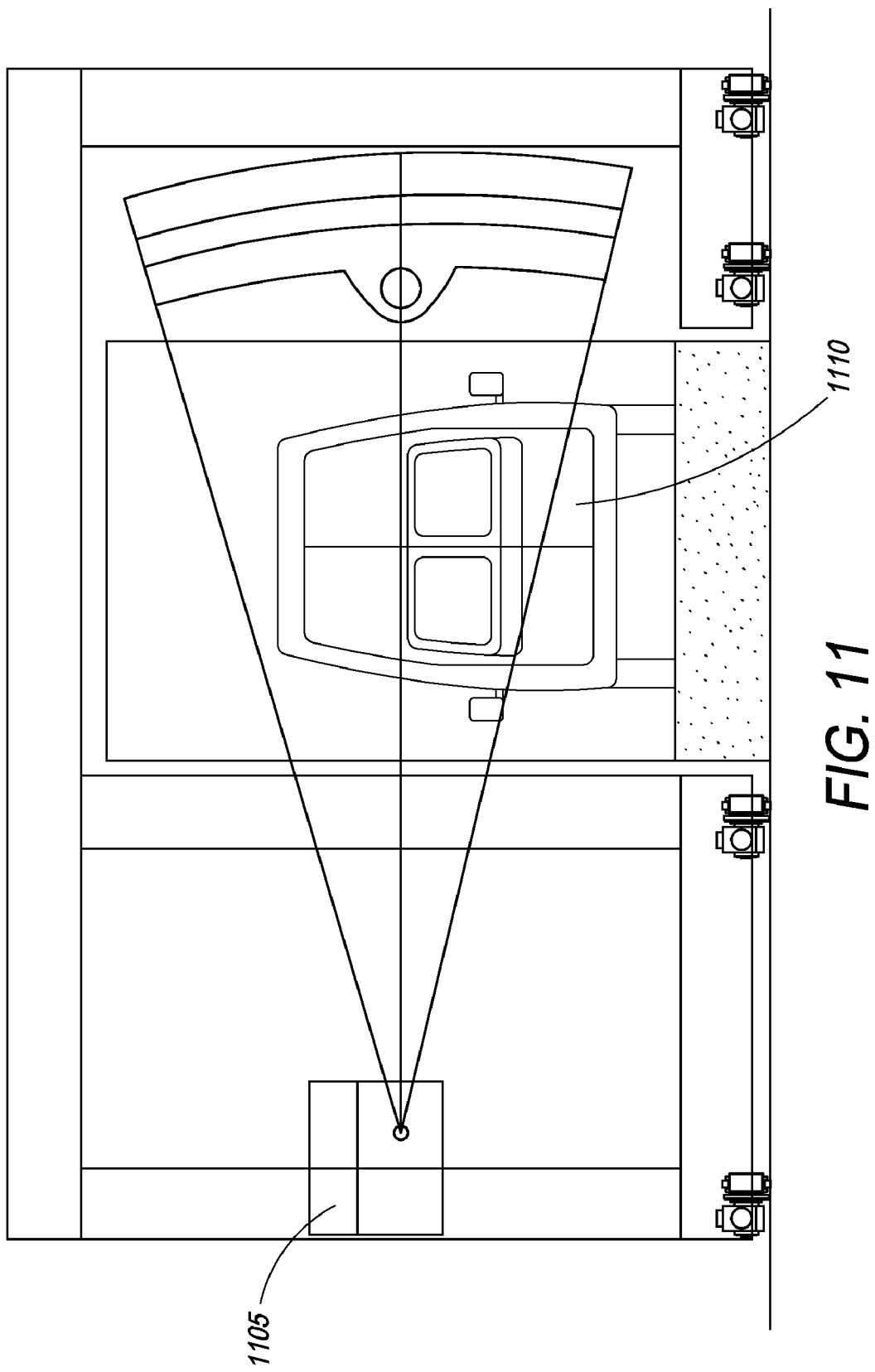
FIG. 11 illustrates another embodiment of the multiple pass inspection system of the present invention wherein the source is vertically positioned to completely scan an object under inspection in a dual pass scan configuration, wherein the first pass is shown in FIG. 10.

FIG. 11 illustrates another embodiment of the multiple pass inspection system of the present invention wherein the source is vertically positioned to completely scan an object under inspection in a dual pass scan configuration, wherein the first pass position is shown in FIG. 10. Thus, if a single pass can is not sufficient to cover the entire volume of the object under inspection, the source 1105 can be vertically positioned at a second point that is most favorable to allow for coverage of the remainder of the object under inspection 1110—that portion not scanned in the first pass—of the object under inspection 1110. In this embodiment, an upper scan is not required since the lower scan and central scan are sufficient to image the entire object under inspection 1110.

The above examples are merely illustrative of the many applications of the system of present invention. Although only a few embodiments of the present invention have been described herein, it should be understood that the present invention might be embodied in many other specific forms without departing from the spirit or scope of the invention. For example, other configurations of cargo, tires, tankers, doors, airplane, packages, boxes, suitcases, cargo containers, automobile semi-trailers, tanker trucks, railroad cars, and other similar objects under inspection can also be considered. Therefore, the present examples and embodiments are to be considered as illustrative and not restrictive, and the invention is not to be limited to the details given herein, but may be modified within the scope of the appended claims.

I claim:

1. An inspection system for inspecting vehicles and their cargo, comprising:
   a radiation source attached to a gantry, wherein said radiation source is adapted to move in a vertical direction and wherein, after movement in a vertical direction, said radiation source is adapted to rotate in a range of 0 to 90 degrees; and
   a detector array, wherein said detector array pivots around an axis to maintain alignment with said radiation source after movement of said radiation source.

2. The inspection system of claim 1, wherein said radiation source is an X-ray source.

3. The inspection system of claim 1, wherein said radiation source is a gamma source.

4. The inspection system of claim 1, wherein said radiation source is a linear accelerator.

5. The inspection system of claim 1, wherein the detector array is rotated about an axis and wherein said rotation of the detector array aligns the detector array with the radiation source during operation of the radiation source.

6. The inspection system of claim 1, wherein the gantry is moveable.

7. The inspection system of claim 1, wherein the radiation source is adapted to conduct a first scan of an object at a first vertical position and at a first scanning angle and, after completion of said first scan, is adapted to move to a second vertical position and rotate in a range of 0 to 90 degrees.

8. The inspection system of claim 7, wherein, after the radiation source moves to a second vertical position and rotates in a range of 0 to 90 degrees, the radiation source conducts a second scan at a second scanning angle.

9. The inspection system of claim 8, wherein the first scanning angle is different from said second scanning angle.

10. The inspection system of claim 8, wherein the first scan generates a first scanning region, wherein the second scan generates a second scanning region, and wherein the first scanning region is different from the second scanning region.

11. The inspection system of claim 7, wherein the first scan produces an image of the object, wherein said image includes a width of the object of up to 3 meters and a height of the object of up to 2 meters.

12. The inspection system of claim 7, wherein the radiation source moves to a second vertical position and rotates in a range of 0 to 90 degrees to conduct a second scan at a second scanning angle if the object is taller than 2 meters.

13. The inspection system of claim 7, wherein the detector array aligns the detector array with the radiation source during the first scan.

14. The inspection system of claim 8, wherein the detector array is adapted to rotate about an axis and wherein said rotation of the detector array aligns the detector array with the radiation source during the second scan.

15. The inspection system of claim 7, wherein the gantry has a bottom, middle, and top.

16. The inspection system of claim 7, wherein the first vertical position is at the bottom of the gantry.

17. The inspection system of claim 8, wherein the gantry has a bottom, middle, and top.

18. The inspection system of claim 8, wherein the second vertical position is at the middle of the gantry or at the top of the gantry.

19. An inspection system for inspecting vehicles and their cargo, comprising:
 a radiation source attached to a gantry, wherein said radiation source is adapted to move in a vertical direction and wherein, after movement in a vertical direction, said radiation source is adapted to rotate in a range of 0 to 90 degrees; and
 a detector array, wherein said detector array pivots around an axis to maintain alignment with said radiation source after movement of said radiation source, wherein the radiation source is adapted to conduct a first scan of an object at a first vertical position and at a first scanning angle and, after completion of said first scan, is adapted to move to a second vertical position and rotate in a range of 0 to 90 degrees.

20. The inspection system of claim 19, wherein, after the radiation source moves to a second vertical position and rotates in a range of 0 to 90 degrees, the radiation source conducts a second scan at a second scanning angle.

* * * * *